United States Patent [19]
Skelton et al.

[11] Patent Number: 5,958,755
[45] Date of Patent: *Sep. 28, 1999

[54] PROCESS OF MAKING FLAVORED YEAST EXTRACTS

[75] Inventors: John Oliver Skelton, Burton upon Trent; Deborah Anne Georgina Anderson, Staffs; John Charles Hobson, Burton upon Trent, all of United Kingdom

[73] Assignee: CPC International Inc., Englewood Cliffs, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/714,971

[22] Filed: Sep. 17, 1996

Related U.S. Application Data

[63] Continuation of application No. 08/382,939, Feb. 1, 1995, abandoned, which is a continuation of application No. 08/160,596, Dec. 1, 1993, abandoned.

[51] Int. Cl.⁶ .................. C12N 1/14; A23C 9/12
[52] U.S. Cl. ............ 435/255.2; 426/62; 426/655; 426/656
[58] Field of Search .................. 435/255.2; 426/62, 426/655, 656

[56] References Cited

U.S. PATENT DOCUMENTS

| | | | |
|---|---|---|---|
| 3,716,379 | 2/1973 | Van Pottelsberghe De La Potterie | 426/62 |
| 4,194,017 | 3/1980 | Poiger et al. | 426/533 |
| 4,243,750 | 1/1981 | Muller et al. | 435/162 |
| 4,303,680 | 12/1981 | Tanekawa et al. | 426/60 |
| 5,011,696 | 4/1991 | Haas et al. | 426/28 |
| 5,073,387 | 12/1991 | Whistler | 426/7 |

FOREIGN PATENT DOCUMENTS

| | | | |
|---|---|---|---|
| 837651 | 2/1939 | France . | |
| 2154646 | 11/1973 | France | C12D 13/00 |
| 2354057 | 6/1977 | France | A23L 1/221 |
| 47003142 | 5/1968 | Japan . | |
| 9116447 | 10/1991 | WIPO | C12P 21/06 |

OTHER PUBLICATIONS

"Use of Yeast Biomass in Food Production" (CRC Press), Halasz and Lasztity, pp. 172–181.
Jwanny et al, J. Basic Microb., 29(9): 581–586 (1989).
Webb, Enzyme Nomenclature, Academic Press, Inc.: New York 1984, pp. 306–310,311.
Vitolo et al, Rv. Farm Boquim. Univ. Sao Paulo, 17(1): 86–92 (1981).

*Primary Examiner*—Irene Marx
*Attorney, Agent, or Firm*—Norris, McLaughlin & Marcus

[57] ABSTRACT

Flavored yeast extracts are prepared by incorporating one or more hydrolysates of fruit, vegetable, herb, spice, fungus or mixtures thereof in a yeast autolysis process.

8 Claims, No Drawings

PROCESS OF MAKING FLAVORED YEAST EXTRACTS

This application is a continuation, of application Ser. No. 08/382,939 filed Feb. 1, 1995, now abandoned which in turn is a continuation of application Ser. No. 08/160,596, filed Dec. 1, 1993 both now abandoned.

BACKGROUND OF THE INVENTION

1. Field of the Invention

This invention relates to yeast extracts. In particular, this invention relates to yeast extracts having novel and interesting flavors which are produced by the modification of conventional processes for producing yeast extract.

2. Description of Related Art

Yeast extract is a nutritious palatable paste prepared from brewer's or baker's yeast by autolysis. This process comprises the self-digestion of yeast cells principally through yeast proteolytic enzyme activity so that proteinaceous soluble solids can be recovered and, if desired, concentrated to form a paste.

In conventional processes, yeast is diluted with water to a specified solids content before autolysis. Salt may be added to the resulting slurry to aid cell membrane rupture and to exercise a degree of control over microbial flora. Yeast proteins are solubilized and hydrolysed during the autolysis process. Although the natural yeast enzymes may be sufficient to carry out the hydrolysis, the activity of the yeast proteolytic system may optionally be augmented by the addition of exogenous enzymes.

On completion of the autolytic process, the soluble fraction is harvested and concentrated by a series of evaporation steps to give a typical standard yeast extract. The autolytic process typically solubilizes around 62% of the starting total yeast solids and yields a maximum of 80% of the yeast's original protein content.

WO 91/16447 discloses a process for producing yeast extracts in which the autolysis process is carried out on a mixture of yeast and non-yeast protein source such as gluten, bran or soya bean meal. The process relies upon the yeast proteolytic system or an exogenous proteolytic enzyme to break down the non-yeast protein source.

U.S. Pat. No. 4,194,017 describes the production of meat flavored products by the steam distillation of treated yeast extract and the reaction of the residue following distillation with a vegetable protein hydrolysate, a monosaccharide and a sulphur-containing substance. The resulting product is claimed to be free from any aftertaste from either the yeast extract or the hydrolysate.

JP 72-03142 teaches a method for eliminating yeast and amino acid odors from yeast extract by heating the extract in the presence of enzymatically hydrolysed vegetable protein.

It has now been found that a range of yeast extract-based products having a variety of novel and interesting flavors may be produced which, as a result of the diversity of their flavors, have many potential applications in areas where the use of conventional yeast extracts is inappropriate. Since yeast extract is highly nutritious, the ability to tailor its taste to suit different requirements or personal preferences either as an additive to other foodstuffs or as a product per se is highly beneficial.

This invention allows the production of flavored yeast extracts by the use of naturally occurring plant or fungal material by modification of the conventional yeast autolysis process.

SUMMARY OF THE INVENTION

Accordingly, the present invention provides a method for producing a comestible product comprising:

(i) providing a slurry comprising yeast cells and water;

(ii) maintaining the slurry at a temperature and for a period of time sufficient to effect at least partial enzymatic hydrolysis of the yeast cells;

(iii) separating the water-soluble fraction from the resulting mixture; and (iv) concentrating the water-soluble fraction;

wherein one or more hydrolysates of fruit, vegetable, herb, spice, fungus or mixtures thereof are present in the slurry, the mixture or the water-soluble fraction before, during or after steps (i) to (iii).

In a further embodiment, the invention provides a comestible product comprising the mixture obtained from a process comprising the formation and autolysis of an aqueous yeast slurry and the separation and concentration of the resulting water-soluble fraction wherein at least a part of said process is carried out in the presence of one or more hydrolysates of fruit, vegetable, herb, spice, fungus or mixtures thereof.

DETAILED DESCRIPTION OF THE INVENTION

The hydrolysates used in the present invention are derived from substrates which are principally carbohydrate in nature and are preferably produced enzymatically. Unlike the process disclosed in WO 91/16447, their hydrolysis is not dependent on the proteolytic system of yeast (or of the added exogenous enzyme) although this system may be involved in the breakdown of the hydrolysates during the process of the invention. Suitable hydrolysates may be produced, at least partially, by the action of one or more carbohydrase enzymes on the substrate, which may have been mechanically broken down to some extent (e.g., comminuted by mincing) in order to assist the solubilization of the plant or fungus derived carbohydrates. The hydrolysis may be augmented by simultaneous or sequential protease treatment. The substrates for hydrolysis are edible fruit, vegetables, herbs, spices, fungi or mixtures thereof and include plum, apple, pear, raspberry, apricot, strawberry, celery, carrot, turnip, leek, onion, tomato and mushroom. The hydrolysates may be prepared from a single substrate or from a mixture of two or more substrates and may be used in the process of the invention either singly or as a mixture of two or more hydrolysates.

The hydrolysates are preferably added before, during or after step (i) of the process so that they are present in the mixture during the hydrolysis of the yeast cells. However, the hydrolysates may also be added after the yeast autolysis is complete, following separation of the water-soluble fraction, for example.

In another embodiment of the present invention, the hydrolysates are produced in situ by the inclusion of the fruit, vegetable, herb, spice, fungus (or mixtures thereof) substrates in whole or at least partially comminuted form in the slurry together with at least one suitable carbohydrase enzyme in order to effect co-hydrolysis of yeast and substrate during the process of the invention.

The plant or fungal materials used as substrates in the present invention may be fresh or may have been modified. The plant or fungal material may have been modified by drying, freezing or canning treatments, for example. Preferably, the amount of substrate or hydrolysate is such that the mixture of yeast and non-yeast solids prior to step (iii) of the process contains from 5% to 65% by weight non-yeast solids based on the total weight of yeast and non-yeast solids.

The preferred sources of yeast cells for use in the present invention are brewer's yeast and baker's yeast. These may be provided in a number of forms (such as dried yeast) but a particularly preferred source is brewer's yeast in the form of a slurry or cream obtained directly from the brewer. Step (i) of the process of the invention may be carried out by the addition of a suitable aqueous liquid (e.g., water) to the yeast cells or may be effected by altering, if necessary, the amount of water in the slurry or cream obtained from the brewer. Typically, a 14 to 18% yeast solids slurry obtained from the brewer or a batch of pressed baker's or brewer's yeast containing 22% to 35% solids is diluted to give a 10 to 14% total solids slurry (e.g., about 12% total solids).

Step (ii) of the process preferably involves autolysis of the yeast cells. This can be carried out by methods well-known to those skilled in the art such as that described in WO 91/16447. Generally, the process involves maintaining the mixture at a temperature of from 40° C. to 65° C. for from 6 to 20 hours. Exogenous enzymes (e.g., those having proteolytic activity, such as papain) may be added to the mixture in order to augment the activity of the yeast proteolytic enzymes. The autolysis may be carried out in the presence of up to 1% by weight sodium chloride preferably by its inclusion in the slurry. Sodium chloride aids plasmolysis of the yeast cells and inhibits the growth of microbial flora. Although the process of the present invention may be carried out under various conditions well-known to those skilled in the art of making yeast extract, the slurry is preferably maintained (i) at 40° C. to 50° C. for 5 to 15 hours (e.g., around 47° C. for about 10 hours); then (ii) at 55° C. to 65° C. for 1 to 5 hours (e.g., around 60° C. for about 2 hours); and (iii) at a temperature and for a further period of time to pasteurize the mixture and denature the enzymes (e.g., around 90° C. for about 1 hour). It is clear that these conditions may vary depending on whether exogenous enzymes (e.g., carbohydrases and/or proteases) are added to the mixture but the consequent alteration to the conditions would be well-known to those skilled in the art.

Step (iii) of the process involves separation of the fraction containing soluble solids from the crude hydrolysis mixture. The separation can be achieved by conventional methods for separating soluble solids from crude yeast hydrolysate mixtures in the production of standard yeast extracts by autolysis. Hence, in the present invention the soluble fraction may be obtained by centrifugal separation and filtration. The resulting soluble fraction from the hydrolysis process is concentrated preferably by evaporation to, for example, about 40 to 50% total solids and the concentrate used as a base for process flavoring agents usually produced by controlled Maillard reactions. The soluble fraction from the hydrolysis process may, alternatively, be concentrated by evaporation to form pastes containing from 55 to 80% total solids, preferably from 70 to 80% (e.g., around 75%) total solids. Salt or other additives may optionally be added before the evaporation steps as is conventional in standard yeast extract processes.

Presently preferred substrates for use in the present invention are celery, carrot, turnip, leek and onion which may be hydrolysed individually or as a mixture. The incorporation of such a mixed hydrolysate prior to the yeast autolysis procedure has been found to impart surprisingly pleasant, unique and savory flavor notes to the yeast extract products.

By selecting appropriate fruit, vegetable, herb, spice and fungal sources for use as enzymatic hydrolysates or in unhydrolysed form for the formation of hydrolysates in situ, the flavor of yeast extract may be modified to dramatically extend the range of flavored yeast extracts available. Such flavors are useful in altering the flavor characteristics of the yeast extract itself, but also have wider application in the food industry as taste additives, especially where ingredients of a particular character are required. The surprising novel and interesting flavors of the yeast extracts produced in the present invention are believed to be due not only to the specific flavor contribution of the added substance, but also to a synergistic effect between this and the compounds found in yeast extract. It has been found that the extracts of the invention may possess interesting flavors which bear little or no relation to the flavor of the hydrolysate used. The extracts may have flavors which are undesirable in a concentrated form but when the extracts are incorporated in another product in a relatively small amount they impart a desirable flavor to that product. The present invention thus greatly widens the possible applications for yeast extract in food products.

Enzymatic hydrolysates of fruit, vegetable, herb, spice or fungi, can be conventionally prepared using one or more commercially available preparations which exhibit carbohydrase activity. These commercially available enzyme preparations are isolated, purified and concentrated, notably from fungal sources, and may have one principle activity (e.g., a principle cellulase activity). The flavor components of such enzymatic hydrolysates may be modified in the process of the invention by reaction with one or more yeast-derived products resulting from the action of natural yeast enzymes on the yeast. It is believed that flavor modifications during the autolysis procedure may occur as a result of Maillard-type reactions between carbohydrate components of the added enzymatic hydrolysate and amino acid or peptide products of yeast autolysis. Similarly, reactions may occur as a result of adding unhydrolysed fruit, vegetable, herb, spice or fungi together with appropriate carbohydrases to the yeast slurry prior to autolysis. Addition of the hydrolysates after separation of the water-soluble fraction may also result in the development of Maillard-type flavors during subsequent concentration.

Suitable enzymes for the enzymatic hydrolysis of fruit, vegetable, herb, spice or fungi include carbohydrases, in particular cellulases, hemi-cellulases, pectinases and endogalacturonases. Such enzymes may be used individually or added as a mixture. The enzyme or enzymes may be added in varying amounts but are preferably added in an amount of from 0.1% to 5% of the substrate dry solids when suspended in water at a concentration of between 5% and 50% total solids. The whole is then incubated for between 2 and 30 hours more preferably between 5 and 20 hours and most preferably between 13 and 16 hours at a temperature of between 25° C. and 85° C., more preferably between 30° C. and 60° C., most preferably between 40° C. and 50° C. This may be followed by incubation for between 5 and 60 minutes preferably 20–40 minutes at a temperature of between 80° C. and 100° C., preferably between 90° C. and 95° C. to terminate enzyme activity. An alternative to the last step is to allow the enzymatically treated material to flow through a heated chamber or pipe, which may be followed by passage through a cooled chamber or pipe. The temperature of the heated chamber or pipe is maintained at about 60° C., preferably above 80° C., and that of the cooled chamber or pipe below 80° C. and preferably below 60° C. Enzymatically treated material would be caused to flow through the chambers or pipes at such a velocity that it resides within each chamber or pipe for a relatively short time, typically between 1 second and 5 minutes. Within the heated chamber or pipe the temperature would be adjusted to cause the residual enzyme activity of the fluid to cease, without unpleasant burnt flavor notes developing, during the period of time the fluid takes to pass through the heated chamber or pipe. Typically the maximum temperature of the heated chamber or pipe is 125° C. Directly after leaving the heated chamber or pipe, the fluid is caused to pass through the cooled chamber or pipe to rapidly reduce the temperature of the fluid and prevent unpleasant burnt flavors from developing. Typically the residence time within the cooled chamber or pipe might be between 1 second and 5 minutes. Prior to incorporation into the yeast suspension, the resultant enzymatic hydrolysate should be cooled.

The present invention provides yeast extract based products having both novel and interesting flavors that may, in some cases, be described as meaty or savory. As a result of the novel flavors possessed by these products, there are many potential applications for the products where standard yeast extract would not achieve the same effect. The product may be presented in many forms such as aqueous liquid, paste or dried powder.

The invention will now be described with reference to the following illustrative examples, which are not intended to be limiting.

EXAMPLE 1

200 g of mixed dried vegetable containing celery, carrot, turnip, leek and onion was mixed with 800 g of distilled water. Commercially available enzyme preparation with a significant carbohydrase activity was added at 3% of the dried vegetable weight. The whole was then incubated with stirring at 45° C. for 14.5 hours followed by 95° C. for 30 minutes. This product formed the mixed vegetable enzymatic hydrolysate.

The mixed vegetable enzymatic hydrolysate was mixed with fresh brewer's yeast, water and salt to give a final concentration of 12.7% total solids and 0.7% salt. Three mixtures were prepared containing 10%, 25% and 50% enzymatic hydrolysate solids by weight based on the total weight of yeast and non-yeast solids.

The whole was then autolyzed with stirring at 47° C. for 10 hours followed by 60° C. for 2 hours followed by 90° C. for 1 hour.

The soluble solids fraction was separated and evaporated and the final extract prepared in the manner conventionally used for yeast extract.

All final extracts were found to possess novel and interesting flavors. In particular, it was noted that meaty notes were enhanced by incorporation of the mixed vegetable enzymatic hydrolysate.

EXAMPLE 2

Mixed vegetable enzymatic hydrolysate was prepared as described in example 1. In this case, the product was filtered in order to separate the soluble fraction.

Separately, fresh brewer's yeast at 12.7% total solids and 0.7% salt was autolyzed according to the standard procedure. The soluble solids fraction from the brewer's yeast autolysate was separated by centrifugation.

The soluble solids fractions from each preparation were mixed in proportions containing 10%, 25% and 50% enzymatic hydrolysate solids by weight based on the total weight of soluble yeast and soluble non-yeast solids.

The mixed soluble solids fractions were evaporated and the final extract prepared in the manner conventionally used for yeast extract.

All final extracts were described as very pleasant with a strong vegetable note. In addition, it was noted that the meaty note was less pronounced in comparison with those extracts produced in example 1.

EXAMPLE 3

1141.02 g minced fresh red pepper, capsicum, with the seeds removed was prepared. An enzyme preparation featuring carbohydrase activity was added at a level of 1% of the weight of the minced pepper. The whole was then incubated, with stirring, at 45° C. for 14 hours followed by 95° C. for 30 minutes. The product formed the enzymatic hydrolysate.

The enzymatic hydrolysate was blended with fresh brewer's yeast, in the proportions 25% enzymatic hydrolysate solids: 75% yeast solids. Water and salt, sodium chloride, were also added to produce a final concentration of 12.7% total solids including 0.7% salt.

The whole was autolyzed with stirring in the same manner that is described in example 1, once again the soluble solids fraction was separated and evaporated and the final extract prepared in the manner conventionally used for yeast extract.

At the same time the co-hydrolysate was produced, a conventional autolysate was made, using yeast solids from the same source, to act as a control. A panel of six tasters was invited to describe the flavor of the 100% yeast solids derived material and the following comments were obtained:

Very dry, meaty, slightly gritty, slightly harsh aftertaste, good yeasty flavor, no bitterness.

When the same panel was asked to comment upon the flavor of the co-hydrolysate with fresh red pepper they commented as follows:

Bitter, powdery, slight raw mushroom taste, distinct celery/vegetable note, slightly harsh, very pleasant, savory, roast savory notes, gluey texture in mouth, initial vegetable note, indescribable, astringent and slightly harsh.

A significant crop of new flavor notes seems to have been created but the tasters surprisingly made no mention of red pepper.

EXAMPLE 4

1005.19 g minced apple was prepared and treated in the same way as the minced red pepper material described in example 3, including combination with fresh brewer's yeast, and an extract was produced.

This extract had a unique flavor with significant sweet notes, and the characteristics of roast gravy were also attributed to it.

EXAMPLE 5

1117.08 g minced mushroom was prepared and to this was added 300 g of water as well as the enzyme described in example 3. The material was processed in the same manner as described in example 3 including yeast addition and an extract was produced.

The extract was submitted to the same panel of tasters as in example 3 with reference to the same control product. Their comments on this extract were as follows:

Very sweet, very good flavor, yeasty, slight bakers yeast flavor, gluey, fishy aroma, very smooth, very dark, quite sickly—savory aftertaste, very slight mushroom note, no strong vegetable notes, similar to an industrially produced vegetable extract.

Once again a wide range of flavors, generally related to the substrate, has been observed.

What is claimed is:

1. A method for producing a flavored yeast extract product by the autolysis of brewer's or baker's yeast cells, said method consisting essentially of:
   (i) providing a slurry with 10% to 14% total yeast solids comprising brewer's or baker's yeast cells and water;
   (ii) maintaining the slurry at a temperature of from 40° C. to 65° C. for a period of from 6 to 20 hours to effect autolysis of the yeast cells and thereby to form an autolysate having a water-soluble fraction and water-insoluble fraction;
   (iii) separating the water-soluble fraction from the autolysate; and
   (iv) concentrating the separated water-soluble fraction to form said yeast extract product;
wherein from 10% to 50% hydrolysate solids, by weight based on total weight of soluble yeast and soluble non-yeast solids, of carbohydrase hydrolysates of mixtures of fruit, vegetable, herb, spice or fungus are added prior to yeast autolysis of step (ii) to enhance flavor of said yeast extract product, such that the mixture of yeast and non-yeast solids prior to step (iii) contains from 5% to 65% by weight non-yeast solids based on the total weight of yeast and non-yeast solids, wherein said flavored yeast extract product has flavor that has little or no relation to the flavor of the hydrolysate as a result of synergistic effects between the hydrolysate used and the compounds found in the yeast extract.

2. A method as claimed in claim 1, wherein the carbohydrase hydrolysates are formed in situ by the inclusion of substrates comprising fruit, vegetable, herb, spice, fungus or mixtures thereof suspended in water at a concentration of between 5% and 50% total solids and at least one carbohydrase enzyme in the slurry of step (i), wherein the enzyme is added in an amount of from 0.1% to 5% of dry solids of said substrates.

3. A method as claim 2, wherein the fruit, vegetable, herb, spice or fungus is not comminuted.

4. A method as claimed in claim 2, wherein the fruit, vegetable, herb, spice or fungus is comminuted.

5. A method as claimed in claim 1, wherein the slurry of step (i) contains up to 1% sodium chloride.

6. A method as claimed in claim 1, wherein the water-soluble fraction is concentrated in step (iv) to a paste comprising from 55 to 80% total solids.

7. The method of claim 1 wherein in step (ii) the slurry is maintained at a temperature of from 40° C. to 50° C. for from 5 to 15 hours and then is maintained at from 55° C. to 65° C. for from 1 to 5 hours.

8. A method as claimed in claim 1, said carbohydrase hydrolysates of mixtures of fruit, vegetables, herb, spice or fungus are selected from the group consisting of celery, carrot, turnip, leek, onion and mixtures thereof.

* * * * *